United States Patent
Durrer et al.

(10) Patent No.: US 8,159,658 B2
(45) Date of Patent: Apr. 17, 2012

(54) SYSTEM AND METHOD FOR THE AUTOMATED ANALYSIS OF SAMPLES

(75) Inventors: Fabian Durrer, Rotkreuz (CH); Kurt Schildknecht, Huenenberg (CH); Urs Vollenweider, Thalwil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 233 days.

(21) Appl. No.: 12/772,284

(22) Filed: May 3, 2010

(65) Prior Publication Data
US 2010/0283995 A1 Nov. 11, 2010

(30) Foreign Application Priority Data
May 6, 2009 (EP) .................................... 09159555

(51) Int. Cl.
*G01N 21/00* (2006.01)
(52) U.S. Cl. ........................... 356/73; 356/244; 356/436
(58) Field of Classification Search ............... 356/36–42, 356/72–73, 243.1–243.8, 244–246
See application file for complete search history.

(56) References Cited

U.S. PATENT DOCUMENTS
4,710,458 A 12/1987 Maines
6,399,398 B1 6/2002 Cunningham et al.
2002/0001854 A1 1/2002 Lee
2003/0048432 A1* 3/2003 Jeng et al. ...................... 356/39
2004/0197927 A1 10/2004 Jeng et al.
2005/0057753 A1* 3/2005 Mosley et al. ................. 356/436

FOREIGN PATENT DOCUMENTS
EP 0426967 9/1990
GB 2377016 12/2002
WO 2006/006113 1/2006

OTHER PUBLICATIONS
Partial European Search Report, Application No. 10160790.1-2204, dated Sep. 6, 2010.

* cited by examiner

*Primary Examiner* — Tarifur Chowdhury
*Assistant Examiner* — Tara S Pajoohi
(74) *Attorney, Agent, or Firm* — Barnes & Thornburg LLP

(57) ABSTRACT

The present invention pertains to a system for the automated analysis of samples, comprising: a first optical device including at least one receptacle for receiving at least one of said samples and a receptacle-associated optical unit including at least one receptacle-associated light source for emitting light adapted for determining a color of said sample and generating a light beam for irradiating said sample contained in said receptacle and at least one receptacle-associated light detector for detecting light transmitted through said sample and generating a receptacle-associated detection signal; a second optical device including at least one test element provided with at least one test zone for applying said sample, said test zone being subject to an optically detectable change in response to at least one characteristic of said sample being different from said color and a test element-associated optical unit.

15 Claims, 3 Drawing Sheets

SYSTEM AND METHOD FOR THE AUTOMATED ANALYSIS OF SAMPLES

This U.S. patent application claims priority to European Patent Application No. 09159555.3 filed on May 6, 2009, which is expressly incorporated herein by reference.

TECHNICAL FIELD

The present invention is in the field of medical diagnostics and concerns a system and method for the automated analysis of samples.

BACKGROUND INFORMATION RELATING TO THE INVENTION

In medical diagnostics, it is one of the most common methods to apply body fluids such as urine to test strips provided with test pads containing various dry-chemical reagents which upon re-action with specific analytes in the samples exhibit a concentration-dependent colouring or discolouring. Conventionally, the test strips ("sticks") are manually dipped into the body fluids followed by a visual inspection of the test pads, e.g., in comparing them with colour patterns which at least allow for a clear distinction between normal and pathologic contents of analytes in the body fluids.

In recent years, a strong demand for the automated analysis of body fluids can be observed. This is not only due to the fact that there is an ongoing increase in clinical analyses requiring more cost-efficient processes but also in the aim to enhance re-liability and preciseness of tests in particular at the detection limits of analytes. For this reason, strong efforts have been made to develop new clinical analyzers for the automated analysis of samples. In today's commercially available analyzers the samples are automatically pipetted onto the test pads, followed by a photometric analysis of the test pads. Dependent on the colouring or discolouring of the test pads as a result of chemical reactions between reagents and samples, the light beam incident on the test pads is more or less absorbed. Accordingly, an intensity of the reflected light can be used to detect colouring or discolouring of the test pads, e.g., to determine concentrations of analytes contained in the samples.

In light of the foregoing, it is an object of the invention to provide an improved system and method for the automated analysis of samples such as urine. This object is met by a system and method according to the independent claims of the invention. Preferred embodiments of the invention are given by the features of the dependent claims.

SUMMARY OF THE INVENTION

It is against the above background that the present invention provides certain unobvious advantages and advancements over the prior art. In particular, the inventor has recognized a need for improvements in a system and method for the automated analysis of samples. According to a first aspect of the invention, a new system for the automated analysis of samples is proposed.

The system comprises a first optical device which includes at least one cavity-forming receptacle for receiving at least one of said samples. In one embodiment, the receptacle is made of light-transparent material such as glass. In another embodiment, the receptacle is provided with a portion made of light-transparent material such as glass. The first optical device further includes a receptacle-associated optical unit. The receptacle-associated optical unit includes at least one (first) receptacle-associated light source for emitting light adapted for determining a colour of the sample contained in the receptacle and generating a light beam for irradiating the sample contained in the receptacle. The receptacle-associated optical unit further includes at least one (first) receptacle-associated light detector for detecting light transmitted through the sample contained in the receptacle and generating a (first) receptacle-associated detection signal based upon the transmitted light.

The system further comprises a second optical device which includes at least one test element for receiving the at least one sample adapted to optically detect at least one characteristic of the sample being different from the colour of the sample. The second optical device further includes a test element-associated optical unit for determining the at least one characteristic of the sample and generating a test element-associated detection signal.

In the second optical device, the at least one test element is provided with at least one test zone (e.g. test pad) for applying the sample, wherein the test zone is subject to an optically detectable change in response to the at least one characteristic of the sample being different from the colour of the sample. The test element-associated optical unit includes at least one test element-associated light source for emitting light adapted for determining the optically detectable change of the at least one test zone and generating a light beam for irradiating the test zone. Furthermore, the test element-associated optical unit includes at least one test element-associated light detector for detecting light reflected from the test zone and generating the test element-associated detection signal.

In such test element, the test zone typically is provided with a (e.g. dry-chemical) reagent subject to an optically detectable change in response to the at least one characteristic of the sample. For instance, due to a chemical reaction between the reagent and a reagent-specific analyte contained in the sample, colouring or discolouring of the test zone may occur. Since such chemical reaction is well-known to those of skill in the art, it is not further elucidated herein. According to an embodiment of the system of the invention, the test element may be a container such as a cuvette adapted for centrifuging the sample in order to optically detect centrifugal-force separated components of the sample. The receptacle may particularly be embodied as flow-through cuvette.

The system yet further comprises an analytical unit for analyzing the receptacle-associated detection signal to obtain a first result related to the colour of the sample and for analyzing the test element-associated detection signal to obtain a second result related to the at least one characteristic of the sample being different from the colour.

The system yet further comprises a controlling unit set up to control analysis of the sample. In that, the controlling unit is configured to control activation of the receptacle- and test element-associated optical units and the analyzing unit to analyze the colour of the sample contained in the receptacle and to determine the at least one characteristic of the sample being different from the colour of the sample such as presence, optionally concentration, or absence of at least one analyte contained in the sample. Specifically, the controlling unit is set up to control analysis of the sample in a manner that, based on the first result related to the colour of the sample, a decision is being made whether or not to determine the characteristic of the sample being different from the colour by means of the second device.

It is relevant for the present invention that the colour of the sample can be adequately detected by means of the (first) receptacle-associated light source and the (first) receptacle-associated light detector. This is the case when a spectral component of light generated by the (first) receptacle-associated light source can be selectively absorbed by the sample. Accordingly, the light emitted by the (first) receptacle-associated light source includes a spectral component adapted to be selectively absorbed by the sample. It may also include a spectral component complementary thereto not absorbed by the sample. Stated more particularly, e.g., in case of detecting a yellow colour, a spectral component of light corresponding to blue colour is absorbed by the sample so that the sample appears to have a yellow colour. In one embodiment, the light emitted by the (first) receptacle-associated light source is white light which may be composed of plural light beams generated by plural (first) receptacle-associated light sources the spectra of which add to white light such as a red, green and blue light or may be emitted by one single (first) receptacle-associated light source. In principle the light sources known in the prior art for optical detection purposes are suitable as receptacle-associated light source(s). In one embodiment, white or monochromatic red, green and blue light-emitting diodes which, e.g., can be mounted on a semiconductor circuit board, are used. The receptacle-associated optical unit may further comprise suitable lenses and apertures in addition to the at least one (first) receptacle-associated light source for forming a light beam illuminating the sample contained in the receptacle.

In one embodiment, the (first) receptacle-associated light detector is a wavelength-sensitive light detector adapted to determine a spectral characteristic such as a spectral intensity of the transmitted light. Basically, detectors such as semiconductor detectors which are well-known in the prior art can be used provided that light transmitted through the sample leads to a wavelength-sensitive detection signal when the detector is illuminated. Detectors which have their sensitivity maximum in the range of the transmitted light can be used. Optionally it is possible to use filters which allow the transmitted light to pass selectively in order to make the measurement more stable towards the effects of interfering light.

It is further relevant for the present invention that the optically detectable change of the at least one test zone can be adequately detected by means of the test element-associated light source and the test element-associated light detector. This may be the case when a colouring formed in the test zone as a result of a chemical reaction between reagent and sample absorbs light emitted by the test element-associated light source which attenuates the reflected light. However, the converse case is also possible in which a dye whose presence is detected optically is destroyed as a result of the reaction between reagent and sample and the measured signal is a decrease in the attenuation of the reflected light. Accordingly, light emitted by the test element-associated light source includes a spectral component adapted to be selectively absorbed by the test zone dependent on the colouring or discolouring of the test zone. In one embodiment, light emitted by the test element-associated light source is monochromatic light. In another embodiment, light emitted by the test element-associated light source is white light.

In principle the light sources known in the prior art for optical detection purposes are suitable as light source in the test element-associated optical unit. In one embodiment, mono-chromatic light-emitting diodes are used. In another embodiment, white light-emitting diodes are used. The test element-associated optical unit may also comprise suitable lenses and apertures in addition to the at least one test element-associated light source for forming a light beam, e.g., illuminating the at least one test zone of the test element. In one embodiment, the at least one test-element associated light detector is able to detect a spatially, e.g. linearly, resolved intensity of the received light. As test-element associated light detector, e.g., a semiconductor detector, CMOS-detector, CCD-camera, remission photometer which are well-known in the prior art can be used.

In the system of the invention, due to transferring the sample to the receptacle, a comparably large sample volume can be used which advantageously allows for a highly reliable optical determination of the colour of the sample. In that, the colour of the sample can advantageously be determined similar to a visual inspection thereof. Such determination is performed prior to initiating determination of the at least one characteristic of the sample such as presence and/or concentration of at least one analyte in the sample so that such analysis may be selectively adapted or omitted based on the colour determined.

As used herein, the term "light" is intended to encompass wavelength ranges that can be used by optical arrangements which include ultraviolet and infrared light in addition to the visual range. The term "colour" denotes a natural colour of the sample appearing without any colour-forming or colour-destroying chemical reaction of the sample. The term "colouring" denotes forming of a colour of the test zone of the test element due to a specific chemical reaction between reagent and sample, while the term "discolouring" denotes reducing or destroying of a dye-caused colour of the test zone due to a specific chemical reaction between reagent and sample. The term "intensity" denotes the specific gradation of the colour of the sample such as the various gradations of yellow ranging from light-yellow to dark-yellow, e.g., with respect to urine. The intensity of the colour can be described by its spectral composition. Specifically, using a colour space such as RGB or CMYK based on the primary colours red (R), green (G) and blue (B) or cyan (C), magenta (M), yellow (Y) and black (B), colours and intensities of colours, respectively, can be represented as tuples of numbers or colour components. Accordingly, the intensity of the colour of a sample can be described by colour components of the colour space used.

Samples may include body fluids such as blood, serum, urine and cerebrospinal fluid and any other fluid of interest as long as automated analyzing thereof involves determination of a fluid colour and of at least one characteristic of the fluid different from the colour such as presence, optionally concentration, or absence of an analyte contained therein. In one embodiment, the system of the invention is used for analyzing urine.

According to an embodiment of the system of the invention, the first result is related to an intensity of the colour of the sample, wherein the controlling unit is set up to control analysis of the sample in a manner that the characteristic of the sample being different from the colour is determined in case the intensity of the colour is below a first predefined intensity level and is not determined in case the intensity of the colour corresponds to or is above the first intensity level.

According to another embodiment of the system of the invention, the first device comprises means for adding a predefined amount of at least one diluting fluid to the sample, wherein the controlling unit is set up to control analysis of the sample in a manner that the diluting fluid is not added to the sample in case the intensity of the colour is below a predefined second intensity level and is added in case the intensity of the colour corresponds to or is between said second intensity level and said first intensity level. Since the characteristic of the sample is only determined in case the intensity of the colour is below the first intensity level, it follows that the second intensity level is below the first intensity level. Thus only after adding said diluting fluid said characteristic of the sample is determined.

According to another embodiment of the system of the invention, the system includes at least one pipetting unit adapted for transferring the sample to the receptacle and/or for transferring the sample to the test element. The pipetting unit preferably comprises at least one (e.g. modular) pipetting channel for the automated pipetting of fluid provided with a pump and a pump conduit fluidically connecting the pump and a pipetting tip such as a metallic needle, e.g., made of steel for transferring a positive or negative pressure to the pipetting tip. The pump conduit may, e.g., be made of flexible plastic material. The receptacle is fluidically connected to the pump conduit, wherein a first inlet/outlet port of the receptacle may be connected to a tip-sided first portion of the pump conduit and a second inlet/outlet port of the receptacle may be connected to a pump-sided second portion of the pump conduit. In one embodiment, the receptacle is a flow-through cuvette.

According to another embodiment of the system of the invention, the receptacle-associated optical unit is adapted for measuring a turbidity of the sample contained in the receptacle. In this case, the (first) receptacle-associated light detector is adapted to sense a spectral intensity of light transmitted through the sample contained in the receptacle and the analytical unit for analyzing the receptacle-associated detection signal is adapted for determining a spectral intensity of light transmitted through the sample contained in the receptacle. By this measure, determination of the sample colour may be based on the turbidity of the sample to thereby enhance reliability and preciseness of the colour measurement. Stated more particularly, the analytical unit is adapted for analyzing the receptacle-associated detection signal to obtain a third result related to the turbidity of the sample, wherein the controlling unit is set up to control analysis of the sample in a manner that the first result related to the colour, particularly intensity of the colour, of the sample is modified according to a predefined modification rule based on the third result related to the turbidity of the sample.

According to yet another embodiment of the system of the invention, the receptacle-associated optical unit is adapted for measuring a specific weight of the sample contained in the receptacle. In this case, the receptacle-associated optical unit comprises at least one (second) receptacle-associated light source for emitting light adapted for measuring a specific weight of the sample and generating a light beam for irradiating the sample contained in the receptacle. In this case, the receptacle-associated optical unit further comprises at least one (second) receptacle-associated detector for detecting light reflected from a surface of the sample contained in the receptacle and generating another (second) receptacle-associated detection signal. Furthermore, the analytical unit is adapted for analyzing the (second) receptacle-associated detection signal detection signal in order to determine the specific weight of the sample. In this case, in the receptacle-associated optical unit, the at least one (second) receptacle-associated light detector for detecting light reflected from a surface of the sample contained in the receptacle may be able to detect a spatially, e.g. linearly, resolved intensity of the reflected light. Light detectors which are well-known in the prior art can be used provided that light reflected from the sample leads to a detection signal when the detector is illuminated with this light. Detectors which have their sensitivity maximum in the range of the reflected light can be used advantageously. Optionally it is also possible to use filters which allow the reflected light to pass selectively in order to make the measurement more stable towards the effects of interfering light.

According to a second aspect of the invention, a new optical device for the automated analysis of samples is proposed. The optical device comprises at least one receptacle for receiving at least one of the samples embodied as above-detailed in connection with the system of the invention. Specifically, the receptacle is embodied as a flow-through cuvette.

The optical device further comprises an optical unit which includes at least one (first) cuvette-associated light source for emitting light adapted for determining a colour of the sample and generating a (first) light beam for irradiating the sample contained in the receptacle. The optical unit further includes at least one (first) cuvette-associated light detector for detecting light transmitted through the sample and generating a (first) cuvette-associated detection signal. In one embodiment, the (first) cuvette-associated light detector is able to detect a spectral characteristic and (spectral) intensity of light transmitted through the sample. The optical unit further includes at least one (second) cuvette-associated light source for emitting light adapted for determining a specific weight of the sample and generating a light beam for irradiating the sample contained in the receptacle. It further includes at least one (second) cuvette-associated light detector for detecting light reflected from the sample contained in the cuvette and generating a second cuvette-associated detection signal. In one embodiment, the (second) receptacle-associated light detector is able to detect a spatially, e.g. linearly, resolved intensity of light reflected from the sample.

The optical device further comprises an analytical unit for analyzing the (first) cuvette-associated detection signal to obtain a first result related to the colour of the sample and for analyzing the second cuvette-associated detection signal to obtain a second result related to the specific weight of the sample.

The optical device yet further comprises a controlling unit set up to control analysis of the sample.

According to an embodiment of the optical device, the light of the first cuvette-associated light source is also adapted for determining a turbidity of the sample. Furthermore, the analytical unit is adapted for analyzing the first receptacle-associated detection signal to obtain a third result related to the turbidity of said sample. While turbidity may be per se a parameter of interest to be determined, it may also have an influence on the colour of the sample. In particular, in the presence of turbid samples the colour being determined tends to shift towards red; in other words blue is absorbed more than red. Accordingly, the controlling unit is setup to control analysis of the sample in a manner that the first result related to the colour of the sample is modified according to a predefined modification rule based on the third result related to the turbidity of the sample.

According to a third aspect of the invention, a new method for the automated analysis of samples is proposed. The method of the invention which may be executed in the system of the invention as-above detailed comprises a step of providing at least one of the samples in a receptacle which is made of light-transparent material or includes a portion made of light-transparent material.

It comprises a further step of irradiating the sample with at least one (first) receptacle-associated light beam adapted for determining a colour of the sample. The light of the (first) receptacle-associated light beam includes a spectral component which can be selectively absorbed by the sample and, e.g., may also include a complementary spectral component thereof. In one embodiment, the light of the (first) receptacle-associated light beam is white light. In this embodiment, the sample may be irradiated by plural (first) receptacle-associated light beams the spectra of which add to white light such as a red, green and blue light beam. In the latter case, the plural (first) receptacle-associated light beams may irradiate the sample in a simultaneous or consecutive manner as desired.

The method comprises a further step of detecting light transmitted through the sample by a (first) receptacle-associated light detector and generating a (first) receptacle-associated detection signal. The (first) receptacle-associated light detector may, e.g., be able to detect a spectral characteristic and intensity (spectral intensity) of the transmitted light.

The method comprises a further step of analyzing the (first) receptacle-associated detection signal by an analytical unit to obtain a first result related to the colour of the sample.

The method comprises a further step of deciding on basis of the first result related to the colour of the sample whether or not to proceed with a set of steps, in the following denoted as "determination routine" for determining at least one characteristic of the sample being different from the colour of the sample. The determination routine comprises the following steps of:

Applying the sample to at least one test zone of a test element, wherein the test zone is subject to an optically detectable change in response to a characteristic of the sample.

Irradiating the at least one test zone with at least one test element-associated light beam adapted for measuring the optically detectable change of the test zone. The light of the test element-associated light beam includes a spectral component which can be selectively absorbed by the test zone. In one embodiment, the light of the test element-associated light beam is white light.

Detecting light reflected from the test zone by a test element-associated light detector and generating a test element-associated detection signal. In one embodiment, the test element-associated light detector is able to detect a spatially, e.g. linearly, resolved intensity of light reflected from the test zone.

Analyzing the test element-associated detection signal by the analytical unit to obtain a second result related to the at least one characteristic of the sample such as presence and/or concentration of at least one analyte contained in the sample.

The method of the invention for the automated analysis of a sample as-above detailed may include a step of transferring the sample to the receptacle. It may also include a step of transferring the sample to the at least one test zone of the test element.

In above method, a colour of the sample is determined during a first measurement phase and the at least one characteristic of the sample is determined during a second measurement phase provided that it is decided to perform the determination of the characteristic based on the first result related to the colour of the sample. Accordingly, the second measurement phase starts after elapse of the first measurement phase. It may be preferred to transfer the sample into the receptacle prior to starting the first measurement phase and to transfer the sample to the at least one test zone of the test element prior to starting the second measurement phase using a transferring unit such as a pipetting unit. As-above detailed, it may be preferred to cleanse the transferring unit based on a result of the determination of the colour of the sample, wherein extra-cleansing may be performed in case the intensity of the sample colour exceeds a predetermined level.

In the method of the invention, it is judged on basis of a result of the determination of the colour of the sample whether the determination of the at least one characteristic of the sample is performed or not. By this measure time and material (i.e. costs) may advantageously be saved when such analysis is not performed in case of an intense colour of the sample making a reliable analysis rather unlikely.

According to an embodiment of the method of the invention, the receptacle-associated detection signal is analyzed in a manner to obtain a first result related to an intensity of the colour of the sample. Specifically, it is decided to proceed with the determination routine in case the intensity of the colour is below a first pre-defined intensity level and not to proceed with the determination routine in case the intensity of the colour corresponds to or is above the first intensity level.

According to another embodiment of the method of the invention, it is decided to perform a marking step of marking the second result related to the characteristic of the sample being different from the colour of having a reduced reliability in case the intensity of the colour corresponds to or is above a pre-defined third intensity level being lower than the first intensity level and not to perform the marking step in case the intensity of the colour is below the third intensity level.

According to another embodiment of the method of the invention, the determination routine is modified according to a second predefined modification rule based on the first result related to the colour of the sample. By this measure, e.g., predetermined analysis steps may be omitted or added in case an intensity of the sample colour exceeds a predetermined level.

According to another embodiment of the method of the invention, it is decided to perform a dilution step of adding a pre-defined amount of at least one diluting fluid to the sample prior to performing the determination routine in case the intensity of the colour corresponds to or is above a pre-defined second intensity level being lower than the first intensity level and not to perform the dilution step in case the intensity of the colour is below the second intensity level. Specifically, the fluid is used to dilute the sample in case an intensity of the sample colour exceeds a predetermined level in order to enhance reliability of the determination of the at least one characteristic of the sample. Fluids used for addition to the sample may include water, buffer and any other fluid as long as the desired effect, e.g., diluting the sample, can be obtained.

According to another embodiment of the method of the invention, it comprises a further step of determining a turbidity of the sample to obtain a third result related to the turbidity of the sample, wherein the first result related to the colour of the sample is modified according to a predefined first modification rule based on the third result related to the turbidity of the sample. Specifically, determination of the colour of the sample is based on the turbidity of the sample in order to enhance reliability of the colour determination. In that embodiment, the light of the (first) receptacle-associated light beam transmitted through the sample may be analyzed by the (first) receptacle-associated light detector to determine turbidity of the sample.

According to another embodiment of the method of the invention, it comprises a further step of determining a specific weight of the sample contained in the receptacle. In that case, the method comprises a step of irradiating the sample with at least one (second) receptacle-associated light beam adapted for deter-mining a specific weight of the sample and a step of detecting light reflected by the sample by at least one (second) receptacle-associated light detector and generating a (second) receptacle-associated detection signal. The (second) receptacle-associated light detector for detecting light reflected from a surface of the sample contained in the receptacle may be able to detect a spatially, e.g. linearly, resolved intensity of the reflected light. Also in that case, the method comprises a step of analyzing the (second) receptacle-associated detection signal by an analytical unit to determine a specific weight of the sample.

According to another embodiment of the method of the invention, in case of not performing the determination routine, the receptacle is (extra-)washed in a manner to avoid sample carry-over with respect to the analysis of another sample.

According to another embodiment of the method of the invention, in case of not performing the determination routine, at least a sample-contacted portion of a pipetting unit used for transferring the sample to the receptacle and/or for transferring the sample to the at least one test zone is (extra-) washed in a manner to avoid sample carry-over with respect to the analysis of another sample.

According to another embodiment of the method of the invention, a sample-specific flag is set in response to the first result related to the colour of the sample. The flag is selectively chosen from a set of flags and instructs one or more options selected from the group of options consisting of performing the above-detailed determination routine, omitting the determination routine, modifying the determination routine, performing the above-detailed dilution step, performing the above-detailed marking step, performing the above-detailed receptacle washing step and performing the above-detailed pipetting unit washing step. While flags instructing the above options are explained for the purpose of illustration only, those of skill in the art will appreciate that flags instructing options other than those specified herein can be envisaged.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

Other and further objects, features and advantages of the invention will appear more fully from the following description. The accompanying drawings, which are incorporated in and constitute a part of the specification, illustrate a preferred embodiment of the invention, and together with the general description given above and the detailed description given below, serve to explain the principles of the invention. The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE DRAWINGS

In order that the invention may be more readily understood, reference is made to the following examples, which are intended to illustrate the invention, but not limit the scope thereof.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

The present invention will be described in detail below with reference to the accompanying drawings, where like designations denote like or similar elements.

Figure 1:
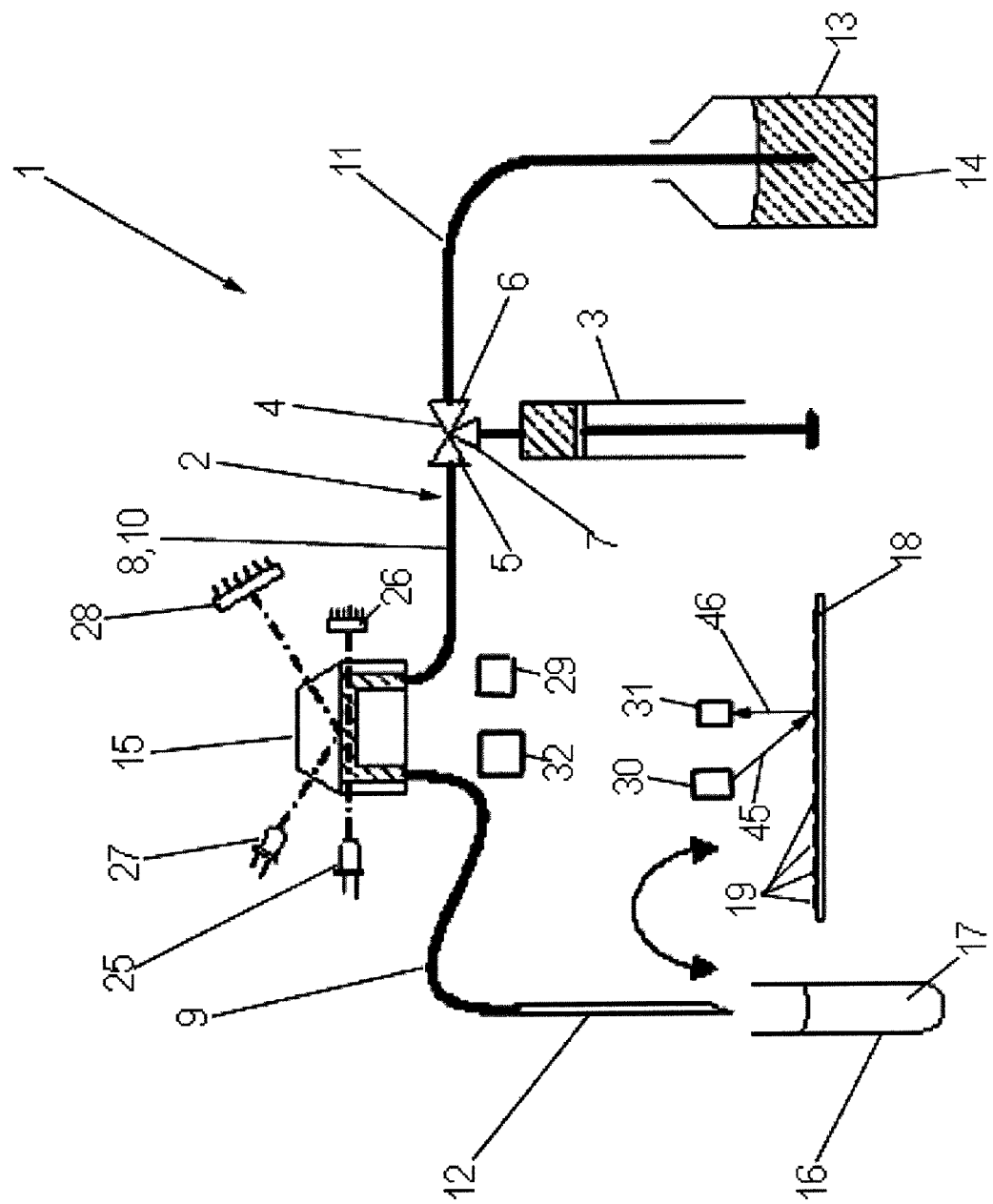
FIG. 1 is a schematic diagram of an exemplary embodiment of the system of the invention for the automated analysis of samples.
Figure 2:
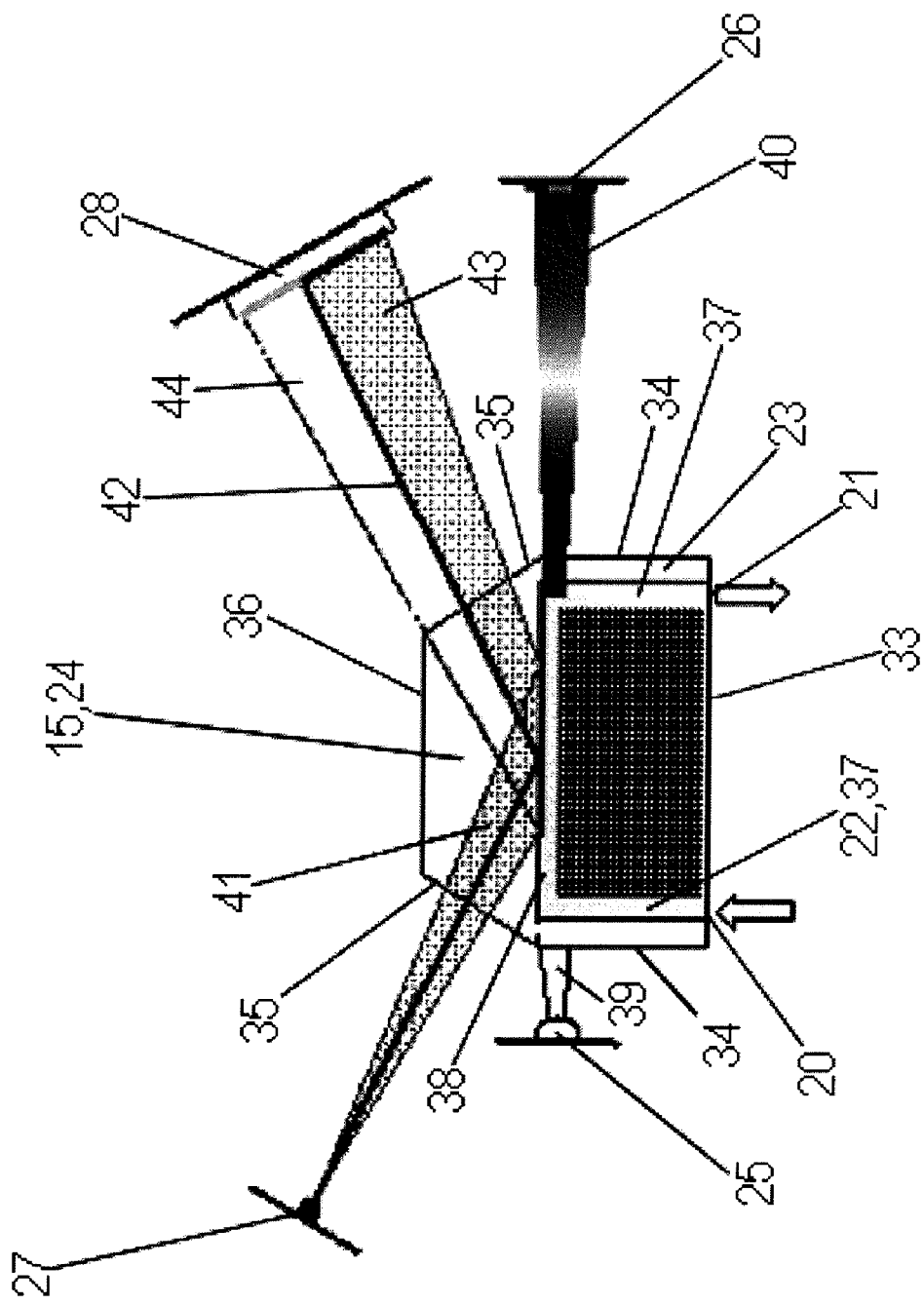
FIG. 2 depicts an enlarged view of a detail of the system of FIG. 1 including the flow-through cuvette.

Referring to FIGS. 1 and 2 an exemplary embodiment of a system 1 for the automated analysis of samples 17, e.g. containing urine, is explained. While only one single sample 17 is depicted in FIG. 1, it is to be appreciated that a plurality of samples 17 can be analyzed by the system 1.

The system 1 is provided with at least one pipetting unit 2 which includes a pump 3 that, e.g., may be embodied as pump of the plunger or membrane pump type and, e.g., can be operated in both directions. The pump 3 is fluidically connected to a first valve port 5 of a 3/2-fluid valve 4. The fluid valve 4 is further provided with a second valve port 6 fluidically connected to a pipetting tip 12 such as a metallic needle, e.g. made of steel, by means of flexible pump tubing 8 and with a third valve port 7 fluidically connected to a reservoir 13 filled with liquid system fluid 14 by means of flexible reservoir tubing 11. Both the pump and reservoir tubings 8, 11 may, e.g., be made of plastic material. The pump tubing 8 consists of a tip-sided first tubing portion 9 and a reservoir-sided second tubing portion 10 fluidically interconnected by means of a flow-through cuvette 15.

The fluid valve 4 is operatively coupled to the pump 3 so that the valve ports 5-7 can be selectively opened or closed to aspirate or dispense fluid through the pipetting tip 12 or to make liquid system fluid 14 flow through the reservoir and pump tubings 8, 11. Stated more particularly, depending on the pumping direction of the pump 3, a pump-generated positive or negative pressure can be transferred to the pipetting tip 12 to aspirate or dispense a sample 17 such as urine from/to a tube 16 through the pipette tip 12 or to aspirate system fluid 14 from the reservoir 13 to dispense it through the pipette tip 12 to cleanse the pipetting unit 2. Otherwise, due to the bidirectional operability of the pump 3, the system fluid 14 can be moved back and forth in the pipetting unit 2 for aspirating or dispensing the sample 17 through the pipetting tip 12. While a three-port fluid valve 4 is depicted in FIG. 1 for the purpose of illustration only, it is to be appreciated that a fluid valve having a number of ports other than three can also be used.

The pipetting unit 2 may be considered a functional entity for pipetting of fluids and can be modular in construction. While only one pipetting unit 2 is depicted in FIG. 1 for the purpose of illustration only, it is to be appreciated that the system 1 may alternatively comprise more than one pipetting unit 2 in ac-cordance with specific demands for pipetting of the sample 17.

The flow-through cuvette 15 (in the introductory portion denoted as "receptacle") is made of optically transparent material such as glass. It basically consists of a parallelepipedic base portion 23 and a tapered cap portion 24 on top of the base portion 23. The base portion 23 is provided with a planar base face 33 and perpendicular side faces 34 which extend perpendicularly with respect to the base face 33. The cap portion 24 is provided with oblique side faces 35 obliquely extending with respect to the base face 33 and a top face 36 which extends in parallel to the base face 33.

The flow-through cuvette 15 forms an internal fluid conduit, in the following called "cuvette conduit" 22 (hatched in FIG. 1). The cuvette conduit 22 consists of two first conduit portions 37 extending in parallel relationship with respect to each other perpendicularly to the base face 33 and a second conduit portion 38 interconnecting the first conduit portions 37 and extending in parallel to the base face 33. The first conduit portions 37 end in first and second cuvette ports 20, 21, respectively, with the first cuvette port 20 being fluidically connected to the tip-sided first tubing portion 9 and the second cuvette port 21 being fluidically connected to the pump-sided second tubing portion 10. Accordingly, the sample 17 contained in the tube 16 can be aspirated through the pipetting tip 12 to fill the cuvette conduit 22 of the flow-through cuvette 15.

The system 1 comprises a first optical device 47 which includes a receptacle-associated optical unit 49 developed as colorimeter for determining a colour of the sample 17 contained in the cuvette conduit 22 of the flow-through cuvette 15. Stated more particularly, the receptacle-associated optical unit 49 comprises a first receptacle-associated light source 25 for emitting white light such as a diode including beam forming elements (not further detailed) for generating a light beam 39. The light beam 39 is essentially orthogonally incident on the side face 34 of the base portion 23 to propagate through the second conduit portion 38 of the cuvette conduit 22. The receptacle-associated optical unit 49 further comprises a first receptacle-associated light detector 26 (colour sensor) which is arranged in such a manner that a transmitted light beam 40 transmitted through the sample 17 contained in the second conduit portion 38 of the cuvette conduit 22 and leaving the cuvette 15 on the opposite side of the base portion 23 can be detected to thereby generate a first receptacle-associated detection signal. Specifically, the first receptacle-associated light detector 26 can detect a spectral characteristic of the transmitted light beam 40 to enable detection of non-absorbed wavelengths of the incident light beam 39 in order to determine a colour of the sample 17.

The first receptacle-associated light detector 26 can further detect an intensity (spectral intensity) of the transmitted light beam 40 to determine a turbidity of the sample 17 contained in the second conduit portion 38 of the cuvette conduit 22.

The receptacle-associated optical unit 49 is further developed as a refractometer for measuring a specific weight of the sample 17 contained in the cuvette conduit 22 of the flow-through cuvette 15. Stated more particularly, the receptacle-associated optical unit 49 further comprises a second receptacle-associated light source 27 for emitting monochromatic (e.g. red) light such as a diode including beam-forming elements (not further detailed) for generating a light beam 41.

The light beam 41 is essentially orthogonally incident on the oblique side face 35 of the cap portion 24 for reflection by a surface of the sample 17 contained in the second conduit portion 38 of the cuvette conduit 22. The receptacle-associated optical unit 49 further comprises a second receptacle-associated light detector (e.g. line sensor) 28 which is arranged in such a manner that a reflected light beam 42 reflected by the sample 17 contained in the second conduit portion 38 of the cuvette conduit 22 and leaving the cuvette 15 on the opposite side of the cap portion 24 can be detected to thereby generate a second receptacle-associated detection signal. Specifically, the second receptacle-associated light detector 28 is able to detect a spatially, e.g. linearly, resolved intensity of the reflected light beam 42 so as to enable detection of a transition between a dark portion 43 and a bright portion 44 of the reflected light as is typical with refractometric measurements.

The system 1 yet further includes a test strip 18 provided with a plurality of test pads 19 serially arranged with respect to each other on an upper side of the test strip 18 for the application of the sample 17. Individual tests pads 19 are provided with a dry-chemical reagent for reacting with a specific analyte contained in the sample 17 and are subject to an optically detectable change such as a colouring or discolouring dependent on presence and optionally concentration of the analyte contained in the sample 17. Specifically, in order to analyse urine, the test pads 19 may contain reagents to determine presence and optionally concentrations of leykocytes, nitrite, protein, glucose, ketones, uribilinogen, bilirubin, erythrocytes and haemoglobin. The test pads 19 may further allow for a determination of a pH-value of the sample 17.

In order to optically evaluate the test pads 19, the system 1 further includes a second optical device 48 which includes a test element-associated optical unit 50 developed as remission photometer for determining an optical change such as colouring or discolouring of the test pads 19. Stated more particularly, the test element-associated optical unit 50 comprises a test element-associated light source 30 for emitting monochromatic (e.g. red) light such as a diode including beam-forming elements (not further detailed) for generating a light beam 45. Individual test pads 19 can be selectively irradiated by the light beam 45 which is obliquely incident on the test pads 19.

The test element-associated optical unit further comprises a test element-associated light detector (e.g. line sensor) 31 arranged in such a manner that a reflected light beam 46 reflected by individual test pads 19 can be detected to thereby generate a second detection signal. Specifically, the test element-associated light detector 31 can detect a spatially, e.g. linearly, resolved intensity of the reflected light beam 46 so as to enable detection of a transition between dark and bright portions of the reflected light.

The system 1 may further include an automated positioning device (not shown in FIG. 1) for transferring the pipetting tip 12 with respect to the tube 16 and/or the test strip 18. Since such positioning device is well-known to those of skill in the art, it is not further detailed herein.

The system 1 may yet further include another automated posi-tioning device (not shown in FIG. 1) for transferring the test element-associated optical unit 50 with respect to the test strip 18 so as to selectively irradiate individual test pads 19 with the light beam 45.

The system 1 further includes an analytical unit 29 electrically connected to each of the light detectors 26, 28, 31 for analyzing the detection signals in order to determine colour, turbidity and specific weight of the sample 17 contained in the cuvette 15 and to determine an optically detectable change such as a colouring or discolouring of the test pads 19 in response to at least one characteristic of the sample 17 such as presence, optionally concentration, of a specific analyte contained therein.

The system 1 further includes a controlling unit 32 for con-trolling the automated analysis of the samples according to a predetermined process operation plan which, e.g., may be embodied as programmable logic controller running a computer-readable program provided with instructions to perform operations in accordance with the process operation plan. The controlling unit 32 receives information from the different components of the system 1 and generates and transmits corresponding control signals for controlling the components according to the process operation plan. In that, the controlling unit 32 is electrically connected to the system components which require control and/or provide information as specified by the process operation plan which include the pump 3, the fluid valve 4, the light sources 25, 27, 30, the light detectors 26, 28, 31 and the analytical unit 29.

Figure 3:
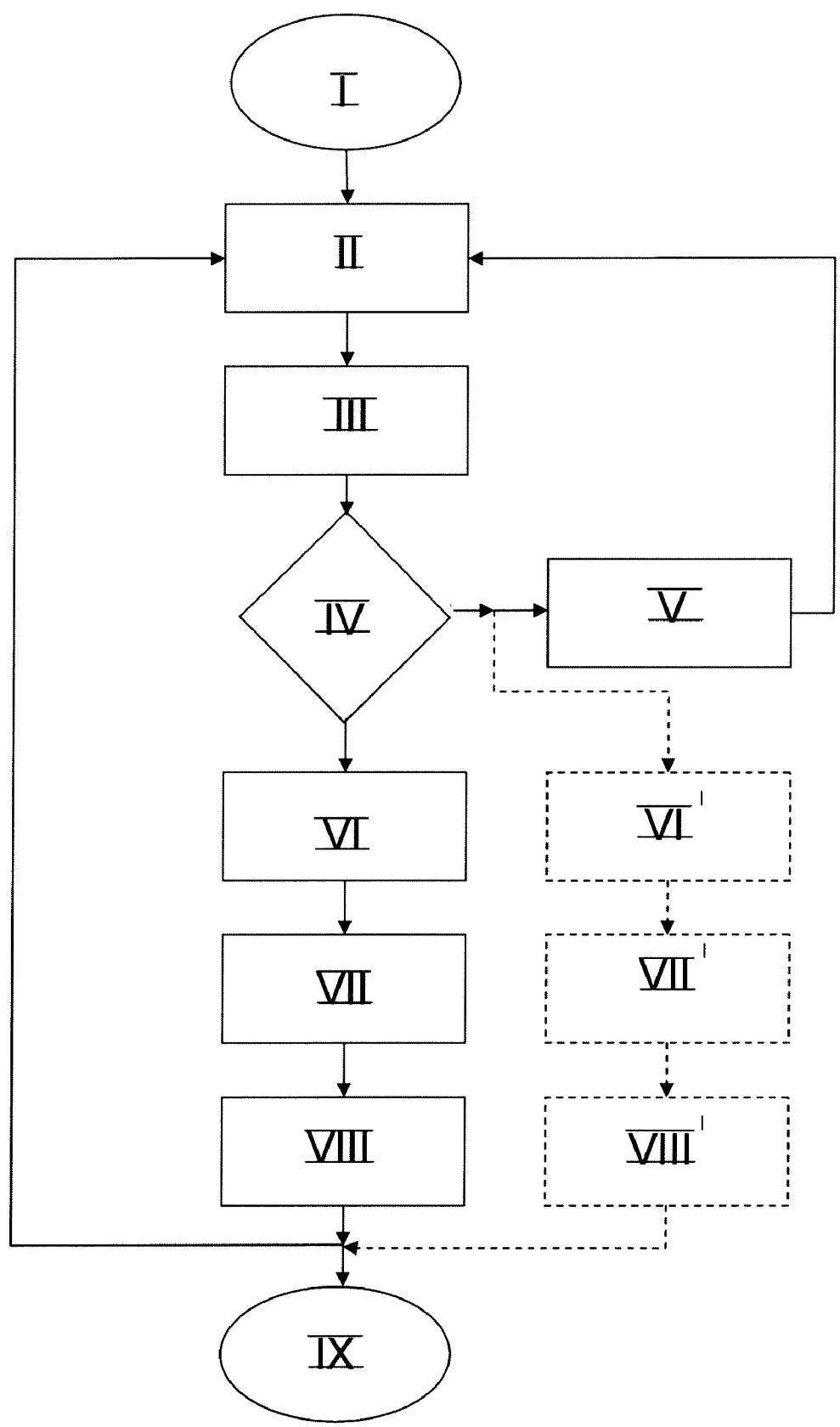
FIG. 3 is a flowchart describing an exemplary embodiment of the method of the invention executed in the system of FIG. 1.

With particular reference to FIG. 3 illustrating a flowchart, an exemplary embodiment of the method for the automated analysis of the sample 17 is explained.

After starting the process (step I), the pipetting tip 12 is dipped into the sample 17 contained in the tube 16 which then is aspirated through the pipetting tip 12 to fill the first tubing portion 9 and the cuvette conduit 22 of the flow-through cuvette 15 with the sample 17 (step II).

Then, both the first receptacle-associated light source 25 and the second receptacle-associated light source 27 are activated to generate light beams 39, 41, one of which passes through the sample 17 contained in the second conduit portion 38 to result in the transmitted light beam 40 and the other one being reflected from the sample 17 contained in the second conduit portion 38 to result in the reflected light beam 42. The transmitted light beam 40 and the reflected light beam 42 are detected by the first receptacle-associated light detector 26 and the second receptacle-associated light detector 28, respectively, to determine colour, turbidity and specific weight of the sample 17 by means of the analytical unit 29 (step III). Specifically, the colour of the sample 17 may be determined based on the turbidity of the sample 17.

Based on the results obtained, it then is checked (step IV) whether an intensity of the colour of the sample 17 exceeds a predetermined level.

If so, the sample 17 is dispensed into a waste container (not shown), followed by extra-washing of the pipetting unit 2 with system fluid 14 by aspirating the system fluid 14 from the reservoir 13 and dispensing the system fluid 14 through the pipetting tip 12 into the waste container to thereby thoroughly cleanse the pipetting unit 2 to avoid any contamination of the next sample (step V). In case another sample 17 is to be analyzed, the process continues with step II to aspirate the next sample 17 through the pipetting tip 12. Otherwise the process terminates (not illustrated).

In the other case, if an intensity of the colour of the sample 17 does not exceed the predetermined level, then aliquots of the sample 17 contained in the cuvette conduit 22 are pipetted onto the test pads 19 of the test strip 18 as illustrated in FIG. 1 (step VI).

After having the sample 17 reacted with reagents contained in the test pads 19, a colouring or discolouring of individual test pads 19 is determined by activating the test element-associated light source 30 to generate the light beam 45 irradiating the test pads 19. Specifically, the emitted light beam 45 is consecutively transferred from one test pad 19 to another to obtain the reflected light beam 46 reflected from each of the test pads 19. The reflected light beam 46 is detected by the test element-associated light detector 31 to determine a colouring or discolouring of the test pads 19, e.g., in accordance with presence and optionally concentration of specific analytes contained in the sample 17 by means of the analytical unit 29 (step VII).

After step VII (or alternatively in parallel with step VII), the pipetting unit 2 is washed in normal manner by aspirating system fluid 14 from the reservoir 13 and dispensing the system fluid 14 through the pipetting tip 12 into the waste container.

After that, in case another sample 17 is to be analyzed, the process continues with step II to aspirate the next sample through the pipetting tip 12. Otherwise the process terminates (step IX).

As an alternative which is illustrated in dashed lines in FIG. 3, in case an intensity of the colour of the sample 17 as determined exceeds the predetermined level, aliquots of the sample 17 contained in the cuvette conduit 22 are pipetted onto all or some predetermined (selected) test pads 19 of the test strip 18 to adapt the analysis to the intensity of the sample colour (step VI'), followed by determining colouring or discolouring of the test pads 19 (step VII').

Optionally, fluid such as buffer can be added to the sample 17 to dilute the sample 17 prior to pipetting aliquots thereof to the test pads 19 in order to enhance reliability of the measurements.

After step VII', the pipetting unit 2 is washed in extraordinary (non-normal) manner by aspirating liquid system fluid 14 from the reservoir 13 and dispensing the system fluid 14 through the pipetting tip 12 into the waste container to thereby thoroughly cleanse the pipetting unit 2 to avoid any contamination of the next sample.

After that, in case another sample 17 is to be analyzed, the process continues with step II to aspirate the next sample through the pipetting tip 12. Otherwise the process terminates (step IX).

Accordingly, in the method of the invention as exemplified in connection with FIG. 3, a colour of the sample 17 can be determined prior to determining at least one characteristic of the sample 17 such as presence and optionally concentration of an analyte contained therein. Hence, analysis of analytes contained in the sample 17 can be stopped based on the result of the determination of the colour of the sample 17, which due to the fact that reliable results concerning analytes may not be obtained in case of an intense colour of the sample 17 advantageously saves costs and time and avoids waste of test strips 18. Otherwise, determination of the at least one characteristic of the sample 17 can be selectively adapted based on the result of the determination of the colour of the sample 17 which allows for reliable results even in case of an intense colour of the sample 17 to thereby save time and costs. Furthermore, additional analytical steps based on the result of the determination of the colour of the sample 17 may be performed. Furthermore, based on the result of the determination of the colour of the sample 17, the pipetting unit 2 can be washed in extraordinary manner to thereby avoid any contamination of the next sample.

Obviously many modifications and variations of the present invention are possible in light of the above description. It is therefore to be understood, that within the scope of appended claims, the invention may be practiced otherwise than as specifically devised. Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

Reference List
1 System
2 Pipetting unit
3 Pump
4 Fluid valve
5 First valve port
6 Second valve port
7 Third valve port
8 Pump tubing
9 First tubing portion
10 Second tubing portion
11 Reservoir tubing
12 Pipette tip
13 Reservoir
14 System fluid
15 Cuvette
16 Tube
17 Sample
18 Test strip
19 Test pad
20 First cuvette port
21 Second cuvette port
22 Cuvette conduit
23 Base portion
24 Cap portion
25 First receptacle-associated light source
26 First receptacle-associated light detector
27 Second receptacle-associated light source
28 Second receptacle-associated light detector
29 Analytical unit
30 Test element-associated light source
31 Test element-associated light detector
32 Controlling unit
33 Base Face
34 Perpendicular side face
35 Oblique side face
36 Top face
37 First conduit portion
38 Second conduit portion
39 Light beam
40 Light beam
41 Light beam
42 Light beam
43 Dark portion
44 Bright portion
45 Light beam
46 Light beam
47 First optical device
48 Second optical device
49 Receptacle-associated optical unit
50 Test element-associated optical unit

The invention claimed is:

1. A system for the automated analysis of samples, comprising:
(a) a first optical device including:
at least one receptacle for receiving at least one of the samples, and
a receptacle-associated optical unit including (i) at least one receptacle-associated light source to generate a light beam to irradiate the sample contained in the receptacle, the light beam of the receptacle-associated light source being adapted for determining a color of the sample, and (ii) at least one receptacle-associated light detector to detect light transmitted through the sample and generate a first detection signal based on the light transmitted through the sample;
(b) a second optical device including:
at least one test element having at least one test zone sized to receive the sample, the test zone being configured to produce an optically detectable change based on at least one characteristic of the sample, the characteristic being different from the color, and
a test element-associated optical unit including (i) at least one test element-associated light source to generate a light beam to irradiate the test zone, the light beam being adapted for determining the optically detectable change of the at least one test zone, and (ii) a test element-associated light detector to detect light reflected from the test zone and generating a second detection signal based on the light reflected from the test zone;
(c) an analytical unit to (i) analyze the first detection signal to determine a first result related to the colour of the sample and (ii) analyze the second detection signal to determine a second result related to the characteristic of the sample; and
(d) a controlling unit electrically-connected to the analytical unit, the controlling unit to control the operation of the analytical unit such that the second detection signal is analyzed in response to the first result related to the colour of the sample.

2. The system of claim 1, wherein the first result is related to an intensity of the colour, and the controlling unit controls the operation of the analytical unit to (i) analyze the second detection signal to determine the second result when the intensity of the colour is less than a first predefined intensity level, and (ii) not analyze the second detection signal to determine the second result when the intensity of the colour corresponds to or is greater than the first intensity level.

3. The system of claim 2, wherein a predefined amount of at least one diluting fluid is added to the sample when the intensity corresponds to or is between a second predefined intensity level and the first predefined intensity level, the second predefined intensity level being lower than the first predefined intensity level, and the controlling unit controls the operation of the analytical unit to analyze the second detection signal to determine the second result after the predefined amount of the diluting fluid is added.

4. The system of claim 1, wherein:
the light beam of the receptacle-associated light source is further adapted for determining a turbidity of the sample,
the analytical unit is configured to analyze the first detection signal to determine a third result related to the turbidity of the sample, and
the controlling unit controls the operation of the analytical unit such that the first result related to the colour of the sample is modified in response to the third result related to the turbidity of the sample.

5. An optical device for the automated analysis of samples, comprising:
(a) at least one flow-through cuvette to receive at least one of the samples;
(b) an optical unit including:
at least one first cuvette-associated light source to emit light adapted for determining a colour of the sample, the first cuvette-associated light source generating a light beam to irradiate the sample contained in the cuvette, at least one first cuvette-associated light detector to detect light transmitted through the sample, the first cuvette-associated light detector generating a first cuvette-associated detection signal, at least one second cuvette-associated light source to emit light adapted for determining a specific weight of the sample, the second cuvette-associated light source generating a light beam to irradiate the sample contained in the cuvette, and at least one second cuvette-associated light detector to detect light reflected from the sample, the second cuvette-associated light detector generating a second cuvette-associated detection signal;

(c) an analytical unit to (i) analyze the first cuvette-associated detection signal to determine a first result related to the colour of the sample and (ii) analyze the second cuvette-associated detection signal to determine a second result related to the specific weight of the sample; and (d) a controlling unit electrically connected to the analytical unit, the controlling unit to control the operation of the analytical unit to analyze the first cuvette-associated detection signal and the second cuvette-associated detection signal.

6. The optical device of claim 5, wherein:

the first cuvette-associated light source is configured to emit light adapted for determining a turbidity of the sample, the analytical unit is configured to analyze the first cuvette-associated detection signal to determine a third result related to the turbidity of the sample, and the controlling unit controls the operation of the analytical unit such that the first result related to the colour of the sample is modified in response to the third result related to the turbidity of the sample.

7. A method for the automated analysis of samples comprising:

irradiating a sample with at least one light beam adapted for determining a colour of the sample;

detecting light transmitted through the sample and generating a first detection signal;

analyzing the first detection signal to obtain a first result related to the colour of the sample; and deciding based on the first result whether to proceed with a determination routine for determining at least one characteristic of the sample, the at least one characteristic being different from the colour, wherein determination routine comprises:

applying the sample to at least one test zone operable to produce an optically detectable change based on at least one characteristic of the sample;

irradiating the test zone with at least one light beam adapted for measuring the optically detectable change of the test zone;

detecting light reflected from the test zone and generating a second detection signal; and analyzing the second detection signal to obtain a second result related to the at least one characteristic of the sample.

8. The method of claim 7, wherein:

the first result is related to an intensity of the colour of the sample, and deciding based on the first result whether to proceed with the determination routine includes (i) determining whether the intensity of the colour is below a first predefined intensity level, and (ii) proceeding with the determination routine when the intensity of the colour is below the first predefined intensity level.

9. The method of claim 8, further comprising:

adding a predefined amount of at least one diluting fluid to the sample when the intensity corresponds to or is between a second predefined intensity level and the first predefined intensity level, the second predefined intensity level being lower than the first predefined intensity level, wherein the predefined amount of the diluting fluid is added prior to proceeding with the determination routine.

10. The method of claim 8, further comprising marking the second result related to the characteristic as having a reduced reliability when the intensity corresponds to or is greater than a third predefined intensity level, the third predefined intensity level being lower than the first intensity level.

11. The method of claim 7, further comprising analyzing the first detection signal to determine the turbidity of the sample, wherein the first result related to the colour of the sample is modified in response to the turbidity of the sample.

12. The method of claim 7, wherein the determination routine is modified in response to the first result related to the colour of the sample.

13. The method of claim 7, further comprising washing the receptacle to avoid sample carry-over with respect to analyzing another sample in response to the first result related to the colour of the sample.

14. The method of claim 7, further comprising washing at least a sample-contacted portion of a pipetting unit to avoid sample carry-over with respect to the analyzing another sample, the pipetting unit being used to move the sample to the receptacle and to move the sample to the at least one test zone.

15. The method of claim 7, further comprising setting a sample-specific flag in response to the first result related to the colour of the sample, the flag instructing one or more options selected from the group of options consisting of performing the determination routine, omitting the determination routine, modifying the determination routine, performing the dilution step, performing the marking step, performing the receptacle washing step, and performing the pipetting unit washing step.

* * * * *